United States Patent [19]

Nelson et al.

[11] 4,035,509
[45] July 12, 1977

[54] METHODS AND COMPOSITIONS FOR THE USE OF 2-CARBOXY-5-OXO-5H-DIBENZO[A,D]CYCLOHEPTENES, SALTS AND ESTERS THEREOF

[75] Inventors: Peter H. Nelson; Karl G. Untch, both of Los Altos, Calif.

[73] Assignee: Syntex (U.S.A.) Inc., Palo Alto, Calif.

[21] Appl. No.: 564,001

[22] Filed: Mar. 31, 1975

Related U.S. Application Data

[63] Continuation-in-part of Ser. No. 463,212, April 22, 1974, abandoned.

[51] Int. Cl.² ............ A61K 31/19; A61K 31/205; A61K 31/235
[52] U.S. Cl. .................... 424/317; 260/211 R; 260/247.2 B; 260/253; 260/268 R; 260/293.62; 260/309.6; 424/316; 260/326.33; 260/429 R; 260/429.9; 260/438.1; 260/439 R; 260/448 R; 260/469; 260/472; 260/501.1; 260/501.11; 260/501.13; 260/501.17; 260/515 R; 424/180; 424/248.55; 424/250; 424/253; 424/267; 424/273; 424/274; 424/287; 424/289; 424/294; 424/295; 536/18; 424/308; 424/310
[58] Field of Search ............ 260/469, 515 R; 424/308, 317

[56] References Cited

U.S. PATENT DOCUMENTS

| | | | |
|---|---|---|---|
| 3,256,335 | 6/1966 | Slates et al. | 260/469 |
| 3,468,939 | 9/1969 | Kaltenbionn | 260/515 |
| 3,600,437 | 8/1971 | Marshall | 260/520 |
| 3,624,142 | 11/1971 | Shen et al. | 260/515 |
| 3,641,134 | 2/1972 | Shen et al. | 260/520 |
| 3,803,234 | 4/1974 | Dostert et al. | 260/469 |
| 3,864,493 | 2/1975 | Cairns et al. | 424/283 |
| 3,879,544 | 4/1975 | Reisner et al. | 424/337 |
| 3,883,593 | 5/1975 | Berezin et al. | 260/590 |
| 3,883,653 | 5/1975 | Barth | 424/251 |
| 3,885,038 | 5/1975 | Pfister et al. | 424/283 |

OTHER PUBLICATIONS

Gomes, C. R. Acad. Sc. Paris, t.274, Serie C, pp. 73–76 (1976).
The Merck Manual, pp. 612–617, 1209–1219 and 1252–1255.
Ebnoether et al., as cited in C.A. 63, 17997 (1965).

*Primary Examiner*—Jane S. Myers
*Attorney, Agent, or Firm*—Alan M. Krubiner; William B. Walker

[57] ABSTRACT

2-Substituted-5-oxo-5H-dibenzo[a,d]cycloheptenes represented by the following formula:

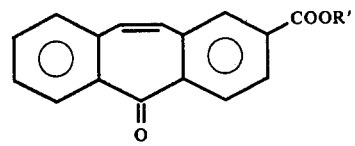

where R' is hydrogen, alkyl having 1 to 12 carbon atoms, or

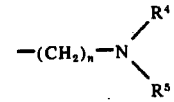

where n is an integer from 2 to 4, inclusive, and $R^4$ and $R^5$ are independently lower alkyl having 1 to 6 carbon atoms or together $R^4$ and $R^5$ and the nitrogen atom to which they are attached form a heterocyclic ring having 5 or 6 total ring atoms; and the pharmaceutically acceptable salts thereof. The compounds are useful in the treatment of auto-immune diseases and allergic reactions.

6 Claims, No Drawings

METHODS AND COMPOSITIONS FOR THE USE OF 2-CARBOXY-5-OXO-5H-DIBENZO[A,D]CYCLOHEPTENES, SALTS AND ESTERS THEREOF

CROSS REFERENCE TO PARENT APPLICATION

This application is a continuation-in-part applicatiion of application Ser. No. 463,212, filed Apr. 22, 1974.

FIELD OF THE INVENTION

This invention relates to novel chemical compounds. More particularly, this invention relates to the novel pharmaceutically active 2-carboxy-5-oxo-5H-dibenzo[a,d]-cycloheptene, and the esters and pharmaceutically acceptable salts thereof.

SUMMARY OF THE INVENTION

The novel 5-oxo-5H-dibenzo[a,d]cycloheptene-2-substituted derivatives of the present invention can be represented by the following formula:

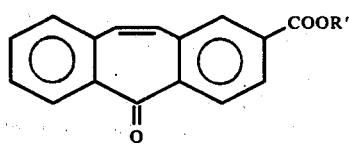

where R' is hydrogen, alkyl having 1 to 12 carbon atoms, or

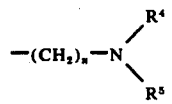

where n is an integer from 2 to 4, inclusive, and $R^4$ and $R^5$ are independently lower alkyl having 1 to 6 carbon atoms or together $R^4$ and $R^5$ and the nitrogen atom to which they are attached form a heterocyclic ring having 5 or 6 total ring atoms; and the pharmaceutically acceptable salts thereof.

As used in this specification and claims, the term "alkyl" refers to both straight and branched alkyl groups having from 1 to 6 or 1 to 12 carbon atoms, as the case may be, and thus includes primary, secondary and tertiary alkyl groups. Typical alkyls include for example, methyl, ethyl, n-propyl, isopropyl, n-butyl, isobutyl, t-butyl, n-amyl, n-hexyl, octyl, decyl, dodecyl, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonia, calcium, magnesium, ferrous, zinc, manganous, aluminum, ferric, manganic salts and the like. Copper salts are also contemplated hereby. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, ethanolamine, lysine, arginine, histidine, caffeine, procaine, N-ethylpiperidine, hydrabamine, choline, betaine, ethylenediamine, glucosamine, methylglucamine, theobromine, purines, piperazine, piperidine, polyamine resins and the like. Isopropylammonium salts are also contemplated hereby.

The compounds of Formula I are useful in the treatment of auto-immune diseases, for example, glomerulonephritis, lupus erythematosus and rheumatoid arthritis, and allergic reactions.

Administration of the active compound of Formula I in an appropriate pharmaceutical composition can be via any of the accepted modes of systemic administration of agents of this type. Thus, administration can be, for example, orally or parenterally, in the form of solid, semi-solid or liquid dosage forms, such as, for example, tablets, suppositories, pills, capsules, powders, liquid solutions, suspensions, or the like, preferably in unit dosage forms suitable for administration of precise dosages. The compositions of this invention will include a conventional pharmaceutical carrier or excipient and an active compound of Formula I, and, in addition, may include other medicinal agents, pharmaceutical agents, carriers, adjuvants, etc.

The preferred manner of administration is oral using a convenient daily dosage regimen which can be adjusted according to the degree of affliction. Generally, a daily dose of from 0.1 mg. to 50 mg. of active compound of Formula I per kilogram of body weight is used, for example, in the range from 1 mg. to 10 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula I may be formulated into a suppository using, for example, polyalkylene glycols, for example, polypropylene glycol, as the carrier. Liquid pharmaceutically administerable compositions can, for example, be prepared by dissolving, dispersing, etc., an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

In the treatment of asthmatic conditions, the compound of Formula I can be administered as above, and, in addition, by inhalation using either solid, liquid, aerosol, or suspensions as the dosage form.

Actual methods of preparing such dosage forms are known, or will be apparent, to those skilled in this art; for example, see Remington's *Pharmaceutical Sciences*, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

5-Oxo-5H-dibenzo[a,d]cycloheptene-2-carboxylic acid can be prepared by esterifying 2-methylterephthalic acid with methanol, in the presence of acid catalyst, to afford the corresponding dimethyl ester which, in turn, is reacted with N-bromosuccinimide to afford 2-bromomethylterephthalic acid dimethyl ester. This diester is reacted with triphenylphosphine to afford, 2,5-bis(carbomethoxy)benzyltriphenylphosphonium bromide which is treated with benzaldehyde and diazabicyclononene to afford, after alkaline hydrolysis, cis and trans stilbene-2,5-dicarboxylic acid. Hydrogenation of this latter compound with hydrogen over a 5% palladium on carbon catalyst affords 2-(2-phenethyl)terephthalic acid. Treatment with polyphosphoric acid yields 5-oxo-5H-dibenzo[a,d]cycloheptane-2-carboxylic acid which can be recrystallized from aqueous dimethylformamide. Treatment of the 5-oxo-5H-dibenzo[a,d]cycloheptane-2-carboxylic acid with diazomethane, N-bromosuccinimide, and dimethylformamide/diazabicyclononene, followed by base hydrolysis and acidification yields 5-oxo-5H-dibenzo[a,d]cycloheptene-2-carboxylic acid.

The free acid can be esterified according to known procedures, for example, by treatment of the free acid or one of its functional derivatives, such as the acid chloride or the acid anhydride, with an appropriate alcohol, in the presence of an acid, dehydrating, or basic catalyst. Other methods of esterification known to those skilled in this art can also be utilized.

Also included within the novel compounds of Formula I are the corresponding dialkylaminoalkyl esters thereof which can be prepared by converting the free acid to the corresponding acid halide, as by treatment with thionyl chloride, and reacting the acid halide so produced with a hydroxyalkylamine, such as 2-dimethylaminoethanol or 2-diethylaminoethanol, to afford the compounds of Formula I wherein R' is

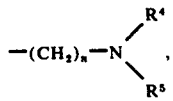

where $R^4$ and $R^5$ are independently lower alkyl. Or, the acid halide derivative can be reacted with a N-(ω-hydroxyalkyl)-heterocyclic amine to afford the compound of Formula I where $R^4$ and $R^5$ and the nitrogen atom to which they are attached for a heterocyclic ring. As used herein, the term "heterocyclic ring" refers to both unsubstituted and substituted heterocyclic rings containing at least one nitrogen ring atom and includes both saturated and unsaturated heterocyclic rings having 5 or 6 ring atoms. More specifically, the heterocyclic rings per se contemplated hereby have one nitrogen atom and four or five carbon atoms, two nitrogen atoms and three or four carbon atoms, or one nitrogen atom one oxygen atom and four carbon atoms. Typical heterocyclic rings include, for example, 2-imidazolin-1-yl, 3-N-methyl-2-imidazolin-1-yl, pyrrolidinyl, 2-methyl-pyrrolidin-1-yl, morpholino, 3-methyl-morpholino, 4-N-methyl-piperazin-1-yl, 4-N-β-hydroxyethyl-piperazin-1-yl, piperidinyl, and the like.

The pharmaceutically acceptable salts are prepared by conventional techniques from pharmaceutically acceptable non-toxic bases, including metal salts such as sodium, potassium calcium, aluminum and the like, as well as from organic amine salts, such as triethylamine, 2-dimethylaminoethanol, 2-diethylaminoethanol, lysine, arginine, histidine, caffeine, procaine, N-ethylpiperidine, hydrabamine salts and the like. Salts with inorganic or organic acids, such as the hydrochloride or maleic acid salts, are also considered to be within the scope of this invention.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the present invention but not specifically described in this specification, will be apparent to those skilled in this art.

Exemplary of the compounds of the present invention, are represented by the structural formula above, are the following illustrative compounds:

2-carboxy-5-oxo-5H-dibenzo[a,d]cycloheptene;
methyl (5-oxo-5H-dibenzo[a,d]cyclohepten-2-yl)carboxylate;
ethyl (5-oxo-5H-dibenzo[a,d]cyclohepten-2-yl)carboxylate;
propyl (5-oxo-5H-dibenzo[a,d]cyclohepten-2-yl)carboxylate;
butyl (5-oxo-5H-dibenzo[a,d]cyclohepten-2-yl)carboxylate;
isopentyl (5-oxo-5H-dibenzo[a,d]cyclohepten-2-yl)carboxylate;
β-N,N-dimethylaminoethyl (5-oxo-5H-dibenzo[a,d]cyclohepten-2-yl)carboxylate;
β-N,N-diethylaminoethyl (5-oxo-5H-dibenzo[a,d]cyclohepten-2-yl)carboxylate;
sodium (5-oxo-5H-dibenzo[a,d]cyclohepten-2-yl)carboxylate;
potassium (5-oxo-5H-dibenzo[a,d]cyclohepten-2-yl)carboxylate; and
calcium (5-oxo-5H-dibenzo[a,d]cyclohepten-2-yl)carboxylate.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

PREPARATION

148 G. of 2-methylterephthalic acid is refluxed for 24 hrs. in 750 ml. of dry methanol containing 30 ml. of sulphuric acid. The solution is cooled, poured into water and extracted with ether. The extract is washed, dried and evaporated to give dimethyl-2-methylterephthalate.

88 G. of dimethyl-2-methylterephthalate in 1000 ml. of carbon tetrachloride containing 89 g. (1 eg.) of N-bromosuccinimide is refluxed for 3 hrs. using a heat lamp. The solution is cooled, filtered and evaporated to dryness to give dimethyl-2-bromomethylterephthalate.

25.7 G. of dimethyl-2-bromomethylterephthalate is refluxed in 250 ml. of acetonitrile containing 26.2 g. (1 eq.) of triphenylphosphine for 4 hrs. The solution is cooled and diluted with 1250 ml. of ether thereby precipitating 2,5-bis(carbomethoxy)-benzyltriphenylphosphonium bromide which is filtered off and dried under vacuum.

51.9 G of 2,5-bis(carbomethoxy)-benzyltriphenyl-phosphonium bromide and 10.6 g. of benzaldehyde are stirred in 300 ml. of acetonitrile and 12.4 g. of diazabicyclononene is added. The mixture is heated briefly to reflux, then cooled and evaporated to an oil. The oil is dissolved in ethyl acetate, and the solution washed with dilute hydrochloric acid, dried and evaporated. The residue is refluxed for 12 hrs. in a solution of 20 g. of potassium hydroxide in 300 ml. of water and 50 ml. or methanol. The solution is cooled and extracted with chloroform. The aqueous solution is acidified with dilute hydrochloric acid and the precipitated cis and trans stilbene-2,5-dicarboxylic acid is filtered off and dried.

23.6 G. of cis and trans stilbene-2,5-carboxylic acid is dissolved in 100 ml. of dimethylformamide containing 500 mg of 5% palladium on carbon and hydrogenated for 2 hrs. The solution is filtered and evaporated to dryness to give a crude product which upon recrystallization from aqueous ethanol yields 2-(2-phenethyl)-terephthalic acid.

23.8 G. of 2-(2-phenethyl)terephthalic acid is dissolved in 200 ml. of sulpholane at 130° C and 150 ml. of polyphosphonic acid is added with stirring. The mixture is stirred at 130° C for 4 hrs., then poured into 1000 ml. of water. The product is filtered off and recrystallized from aqueous dimethylformamide to yield 5-oxo-5H-dibenzo[a,d]-cycloheptane-2-carboxylic acid (m.p. 203°–204° C).

EXAMPLE I 5.0 G. of 5-oxo-5H-dibenzo[a,d]cycloheptane-2-carboxylic acid (as prepared above) is suspended in 50 ml. of dioxane, added to excess ethereal diazomethane, and stirred until dissolution is complete. The solution is then evaporated to dryness to yield 2-carbomethoxy-5-oxo-5H-dibenzo[a,d]cycloheptane.

4.68 G of 2-carbomethoxy-5-oxo-5H-dibenzo[a,d]cycloheptane is refluxed in 100 ml. of carbon tetrachloride containing 3.56 g. (1 eq.) of N-bromosuccinimide while being irradiated with a 100 watt incandescent lamp. After 2 hours the solution is cooled, filtered and evaporated to dryness. The residue is dissolved in 30 ml. of dimethylformamide and 2.48 g. (1eq.) of diazabicyclononene is added. The mixture is heated briefly to 60° C, and water and ethyl acetate are added. The organic layer is washed with dilute hydrochloric acid and water, then dried and evaporated to give 2-carbomethoxy-5-oxo-5H-dibenzo[a,d]cycloheptene. Hydrolysis is eight to one aqueous methanol, 5% potassium hydroxide, followed by acidification with dilute hydrochloric acid yields 5-oxo-5H-dibenzo[a,d]cycloheptene-2-carboxylic acid (m.p. 261°–262° C).

EXAMPLE II 5.0 G. of 2-carboxy-5-oxo-5H-dibenzo[a,d]cycloheptene is dissolved in 100 ml. of chloroform, and 50 ml. of thionyl chloride and 1.0 ml. of dimethylformamide are added thereto. The mixture is left for 3 days, then evaporated to dryness to afford 2-chlorocarbonyl-5-oxo-5H-dibenzo[a,d]cycloheptene. 1.0 G. of this compound is dissolved in 10 ml. of tetrahydrofuran containing 1.0 ml. of isopentyl alcohol and 2 ml. of pyridine. The mixture is left for 24 hours, then evaporated to dryness, dissolved in 1:4 ether/hexane and filtered through silica gel, then evaporated to give isopentyl (5-oxo-5H-dibenzo[a,d]cyclohepten-2-yl)carboxylate (m.p. 26°–30° C).

In similar manner substituting methanol, 2-propanol, ethanol, butanol, 2-butanol, 3-methylbutanol, pentanol, 2-pentanol, 3-pentanol, 3-ethylpentanol, hexanol, 2-hexanol, 3-hexanol, heptanol, 2-heptanol, 3-heptanol, 4-heptanol, octanol, 2-octanol, 4-octanol, nonanol, 4-nonanol, 5-nonanol, decanol, 2-decanol, 3-decanol, 4-decanol, 5-decanol, undecanol, and dodecanol, the corresponding alkyl esters of 2-carboxy-5-oxo-5H-dibenzo[a,d]cycloheptene are obtained, including dodecyl (5-oxo-5H-dibenzo[a,d]cyclohepten-2-yl)-carboxylate (m.p. 46°–48° C).

EXAMPLE III 1.0 G. of 2-chlorocarbonyl-5-oxo-5H-dibenzo[a,d]cycloheptene, as prepared in Example II, is dissolved in 10 ml. of anhydrous tetrahydrofuran with stirring, and treated with 2 ml. of dimethylethanolamine. After the solution is stirred for 16 hours, it is evaporated. The residue is partitioned between ether and dilute hydrochloric acid. The aqueous layer is basified with aqueous ammonia and extracted with ethyl acetate. This solution is evaporated and the residue chromatographed on silica gel, eluting with 10:90:1 methanol:chloroform:-triethylamine, to afford β-N,N-dimethylaminoethyl (5-oxo-5H-dibenzo[a,d]cyclohepten-2-yl)carboxylate as an oil (maleic acid salt: m.p. 132°–135° C).

In similar manner substituting diethylethanolamine for the dimethylethanolamine, there is obtained β-N,N-diethylaminoethyl (5-oxo-5H-dibenzo[a,d]cyclohept-en-2-yl)carboxylate.

Also in similar manner substituting 4-N,N-dimethylaminobutan-1-ol for the dimethylethanolamine there is obtained the corresponding 4'-N,N-diemthylaminobutyl esters, including 4'-N,N-dimethylaminobut-1'-yl (5-oxo-5H-dibenzo [a,d]cyclohepten-2-yl)carboxylate as an oil (maleic acid salt: m.p. 134°–136° C).

EXAMPLE IV

Example III is repeated except 1-β-hydroxyethyl-2-imidazoline; 1-βhydroxyethyl-3-methyl-2-imidazoline; 1-β-hydroxyethyl-pyrrolidine; 1-β-hydroxyethyl-2-methylpyrrolidine; 4-β-hydroxyethylmorpholine; 4-β-hydroxyethyl-3-methylmorpholine; 1-β-hydroxyethyl-4-methyl-piperazine; and 1-β-hydroxyethyl-piperidine; are respectively substituted for the dimethylethanolamine of Example III, to thereby afford β-(2-imidazolin-1-yl)ethyl (5-oxo-5H-dibenzo[a,d]-cyclohepten-2-yl)carboxylate;

β-(3-methyl-2-imidazolin-1-yl)ethyl (5-oxo-5H-dibenzo-[a,d]cyclohepten-2-yl)carboxylate;

β-(pyrrolidin-1-yl)ethyl (5-oxo-5H-dibenzo[a,d]cyclohepten-2-yl)carboxylate as an oil (maleic acid salt: m.p. 136°–138° C);

-(2-methyl-pyrrolidin-1-yl)ethyl (5-oxo-5H-dibenzo-[a,d]cyclohepten-2-yl)carboxylate;

β-(morpholino)ethyl (5-oxo-5H-dibenzo[a,d]cyclohepten-2-yl)carboxylate;

β-(3-methyl-morpholino)ethyl (5-oxo-5H-dibenzo[a,d]-cycloheptene-2-yl)carboxylate; β-(4-methylpiperazin-1-yl)ethyl (5-oxo-5H-dibenzo-[a,d]cyclohepten-2-yl)carboxylate; and β-(piperid-1-yl)ethyl (5-oxo-5H-dibenzo[a,d]cyclohepten-2-yl)carboxylate.

EXAMPLE V 25.0 G. of 2-carboxy-5-oxo-5H-dibenzo[a,d]cycloheptene is added to a mixture of 4.0 g. of sodium hydroxide in 500 ml. of aqueous methanol. The mixture is stirred for 3 hours at room temperature, then the mixture is evaporated to afford sodium (5-oxo-5H-dibenzo[a,d]cyclohepten--yl)carboxylate -yl)-carboxylate (m.p. 300° C). By employing 5.6 g. of potassium hydroxide in place of the sodium hydroxide above, there is obtained potassium (5-oxo-5H-dibenzo[a,d]cyclohepten-2-yl)carboxylate.

EXAMPLE VI 24.0 G. of sodium (5-oxo-5H-dibenzo[a,d]cyclohepten-2-yl)carboxylate in 1000 ml. of water is added to a mixture of 5.55 g. of calcium chloride in 300 ml. of water, and the mixture is allowed to stand for 12 hours at room temperature. The mixture is then filtered, and the filtered salt washed several times with portions of ice cold water. The washed salt is dried under vaccum to yield calcium (5-oxo-5H-dibenzo[a,d]cyclohepten-2-yl)carboxylate.

EXAMPLE VII 0.34 G. of 2-carboxy-5-oxo-5H-dibenzo[a,d]cycloheptene is added to a mixture of 0.32 g. of procaine and 50 ml. of 10% aqueous methanol, and the mixture is stirred for 16 hours at room temperature. The mixture is evaporated under reduced pressure to afford the procaine salt of 2-carboxy-5-oxo-5H-dibenzo[a,d]cycloheptene.

In similar manner, substituting 0.24 g. of lysine, 0.29 g. arginine, 0.32 g. of caffeine, 0.1 g. of ethanolamine, 0.16 g. of 2-(diethylamino)ethanol, 0.15 g. of 2-(dimethylamino)ethanol, 0.32 g. methyl glucamine, or 0.1 g. of ethylenediamine, in place of the procaine above, the corresponding salts of 2-carboxy-5-oxo-5H-dibenzo[a,d]cycloheptene are obtained.

EXAMPLE VIII

The maleic acid salts of Examples III and IV are prepared by dissolving 0.5 g. of the amino ester in 25 ml. ether and adding an ethereal maleic acid solution to the resultant solution until precipitation is complete. The salt is filtered off, washed with ether and dried under vacuum.

EXAMPLE IX 5.0 G. of 5-oxo-5H-dibenzo[a,d]cycloheptene-2-carboxylic acid (as prepared above) is suspended in 50 ml. of dioxane, added to excess ethereal diazomethane, and stirred until dissolution is complete. The solution is then evaporated to dryness to yield methyl (5-oxo-5H-dibenzo[a,d]cyclohepten-2-yl)carboxylate (m.p. 115°–116° C).

EXAMPLE X

The compounds listed in Table I below were tested in the rat passive cutaneous anaphylaxis (PAC) assay with homocyrotropic reaginic antibody and substantially described by I. Mota, *Immunology* 7, 618 (1964).

Normal female rats (Sprague-Dawley) of 150–200 gms. each are passively sensitized at two sites by intradermic injection of rat anti-egg albumin reaginic sera. After 24 hours, each rat is challenged by intraveneous injection of 1 ml. 0.5% Evans blue dye and 1 mg. egg albumin. The test compound is administered either simultaneously with this challenge, or at a measured time interval before challenge (as given in Table I below). The dermic bluing is measured 15 to 25 minutes later. The inhibition of dermic bluing, compared to that of an untreated control, indicates the degree to which the test compound has diminished the anaphylactic reaction.

The above procedure is repeated using other test compounds which are administered orally.

TABLE I

| Test Compound | Dose (mg./rat) | Route of Administration | Time of Administration* | Inhibition of Dermic Bluing |
|---|---|---|---|---|
| 2-carboxy-5-oxo-5H-dibenzo[a,d]-cyclohoptene** | 5 | intravenous | 0 | 100% |
| 2-(pyrrolidin-1-yl)ethyl (5-oxo-5H-dibenzo[a,d]-cyclohepten-2-yl)carboxylate maleic acid salt | 9.3 | intravenous | 0 | 24% |
| 4'-N,N-dimethylamino-but-1'-yl (5-oxo-5H-dibenzo-[a,d]cyclohepten-2-yl)-carboxylate maleic acid salt | 9.3 | intravenous | 10 | 28% |
| methyl (5-oxo-5H-dibenzo-[a,d]cyclohepten-2-yl)carboxylate | 21.2 | oral | 45 | 22% |
| isopentyl (5-oxo-5H-dibenzo[a,d]cyclohepten-2-yl)-carboxylate | 25.6 | oral | 45 | 22% |

*Time (in minutes) before challenge
**Tested as the sodium salt

Inhibition or reaginic antigen-antibody reactions in rats is regarded as representative of inhibition of human reaginic agtigen-antibody reactions which occur during allergic episodes.

EXAMPLE XI

| Ingredients | Quantity per capsule, mgs. |
|---|---|
| 2-carboxy-5H-dibenzo[a,d]-cycloheptene or the sodium salt thereof | 100–200 |
| lactose | 200–400 |

The above ingredients are mixed, then added to a hard-shell gelatin capsule.

EXAMPLE XII

| Ingredients | Quantity per capsule, mgs. |
|---|---|
| 2-carboxy-5H-dibenzo[a,d]-cycloheptene or the sodium | |

| Ingredients | Quantity per capsule, mgs. |
|---|---|
| salt thereof | 120 |
| cornstarch (paste) | 15 |
| magnesium stearate | 0.75 |
| lactose | to 150 |

The active material and the cornstarch (paste) are granulated to 16–20 mesh. The lactose and magnesium sterate are added thereto, thoroughly mixed and then pressed into single scored tablets.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A composition for inhibiting reaginic antigen-antibody reactions in mammals susceptible thereto comprising a pharmaceutically acceptable non-toxic excipient and an effective amount of a compound represented by the formula:

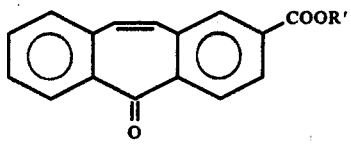

(I)

wherein R' is hydrogen, alkyl having 1 to 12 carbon atoms, or

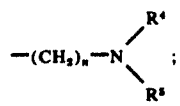

$n$ is an interger from 2 through 4, inclusive; $R^4$ and $R^5$ are independently lower alkyl having 1 to 6 carbon atoms; or a pharmaceutically acceptable salt thereof.

2. The composition of claim 1 wherein said compound is 2-carboxy-5-oxo-5H-dibenzo[a,d]cycloheptene, or a pharmaceutically acceptable salt thereof.

3. The composition of claim 2 wherein said compound is 2-carboxy-5-oxo-5-H-dibenzo[a,d]cycloheptene.

4. A method of inhibiting reagenic antigen-antibody reactions in mammals susceptible thereto which comprises administering to a mammal in need thereof an effective amount of a compound represented by the formula:

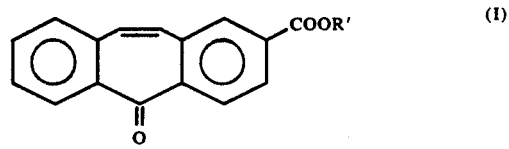

(I)

where R' is hydrogen, alkyl having 1 to 12 carbon atoms, or

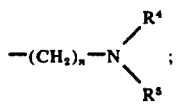

$n$ is an integer from 2 through 4, inclusive; $R^4$ and $R^5$ are independently lower alkyl having 1 to 6 carbon atoms; or a pharmaceutically acceptable salt thereof.

5. The method of claim 4 wherein said compound is 2-carboxy-5-oxo-5H-dibenzo[a,d]cycloheptene, or a pharmaceutically acceptable salt thereof.

6. The method of claim 5 wherein said compound is 2-carboxy-5-oxo-5H-dibenzo[a,d]cycloheptene.

* * * * *